United States Patent
Masumoto

(10) Patent No.: US 6,665,885 B2
(45) Date of Patent: Dec. 23, 2003

(54) GOGGLES

(75) Inventor: Yuusuke Masumoto, Ikoma-gun (JP)

(73) Assignee: Yamamoto Kogaku Co., Ltd., Osaka (JP)

(*) Notice: Subject to any disclaimer, the term of this patent is extended or adjusted under 35 U.S.C. 154(b) by 93 days.

(21) Appl. No.: 09/789,993

(22) Filed: Feb. 20, 2001

(65) Prior Publication Data

US 2002/0023292 A1 Feb. 28, 2002

(30) Foreign Application Priority Data

Feb. 22, 2000 (JP) .................................... 2000-077273

(51) Int. Cl.⁷ .................................................. A61F 9/02
(52) U.S. Cl. ................................................ 2/436; 2/441
(58) Field of Search ........................... 2/436, 437, 426, 2/431, 9, 10, 424, 425, 441, 443

(56) References Cited

U.S. PATENT DOCUMENTS 5,542,130 A * 8/1996 Grabos, Jr. et al. ............ 2/436
5,867,841 A * 2/1999 Chiang ......................... 2/436

FOREIGN PATENT DOCUMENTS

| DE | 150 848 | 9/1981 |
| FR | 2 655 432 | 6/1991 |
| GB | 2 224 134 | 4/1990 |

* cited by examiner

Primary Examiner—Peter Nerbun
(74) Attorney, Agent, or Firm—Koda & Androlia

(57) ABSTRACT

Goggles include a goggle frame and a goggle lens to be detachably fitted in a groove formed on the inner peripheral portion of the goggle frame. The front and rear walls constituting the groove have ventilating openings opposing each other. Either a goggle lens which covers the opening of the rear wall or a goggle lens which allows the openings of the front and rear wall to communicate with each other can be fitted in the groove.

9 Claims, 8 Drawing Sheets

GOGGLES

FIELD OF THE INVENTION

The present invention relates to goggles, and more particularly to goggles used for skiing and snowboarding

PRIOR ART

This type of goggles usually has a ventilation section to prevent inner surfaces of goggle lenses from becoming clouded up with a skier's body temperature, sweating or the like, which allows to avoid accidents due to poor visibility during sliding.

This ventilation section, for example, has a construction in which air is let to be in through holes provided above goggles lenses fitted in a goggle frame. This type of goggles has the following drawbacks; first of all, providing a ventilation section narrows the field of the vision by a certain size. Secondly, anti-fog effect is enhanced in slow and middle-slow sliding such as skiing, however, in case goggles are used under a high speed such as in a downhill race and a jumping race, a large amount of air enters at a high speed from the holes provided above the goggle lenses and this causes problems such as hurting the eyes of a wearer.

Therefore, skiers and the like have desired improvement of goggles in which a wide field of vision can be guaranteed without enlarging goggle frames and the amount of air-flow from ventilation sections can be easily controlled.

SUMMARY OF THE INVENTION

It is, therefore, an object of the present invention to provide goggles in which a wide field of vision can be guaranteed without enlarging goggle frames and the amount of air-flow from ventilation sections can be easily controlled.

Goggles according to the present invention include a goggle frame and a goggle lens detachably fitted into a groove formed on the inner peripheral portion of the goggle frame. The groove of the goggle frame is constituted with a front wall and a rear wall, and the walls are provided with respective ventilation openings which are opposing to each other. The goggles can include either a goggle lens which closes the opening on the rear wall or a goggle lens which allows the openings on the front and rear walls to communicate each other.

The goggle lens which allows the openings on the front and rear walls to communicate in the goggles according to the present invention may have cuttings at the portions corresponding to the openings.

Goggles according to the present invention may further be prepared for with plural goggle lenses having cuttings in varying sizes, so that changing lenses to be fitted in the groove of the goggle frame allows the amount of air-flow into the inside of the goggle lens to be changed.

The opening on the front wall in the goggles according to the present invention may be formed with plural gratings or alternatively covered with a filter.

The embodiments of goggles of the invention stated above will be described below with reference to the accompanying drawings.

DETAILED DESCRIPTION OF THE INVENTION

Figure 1:
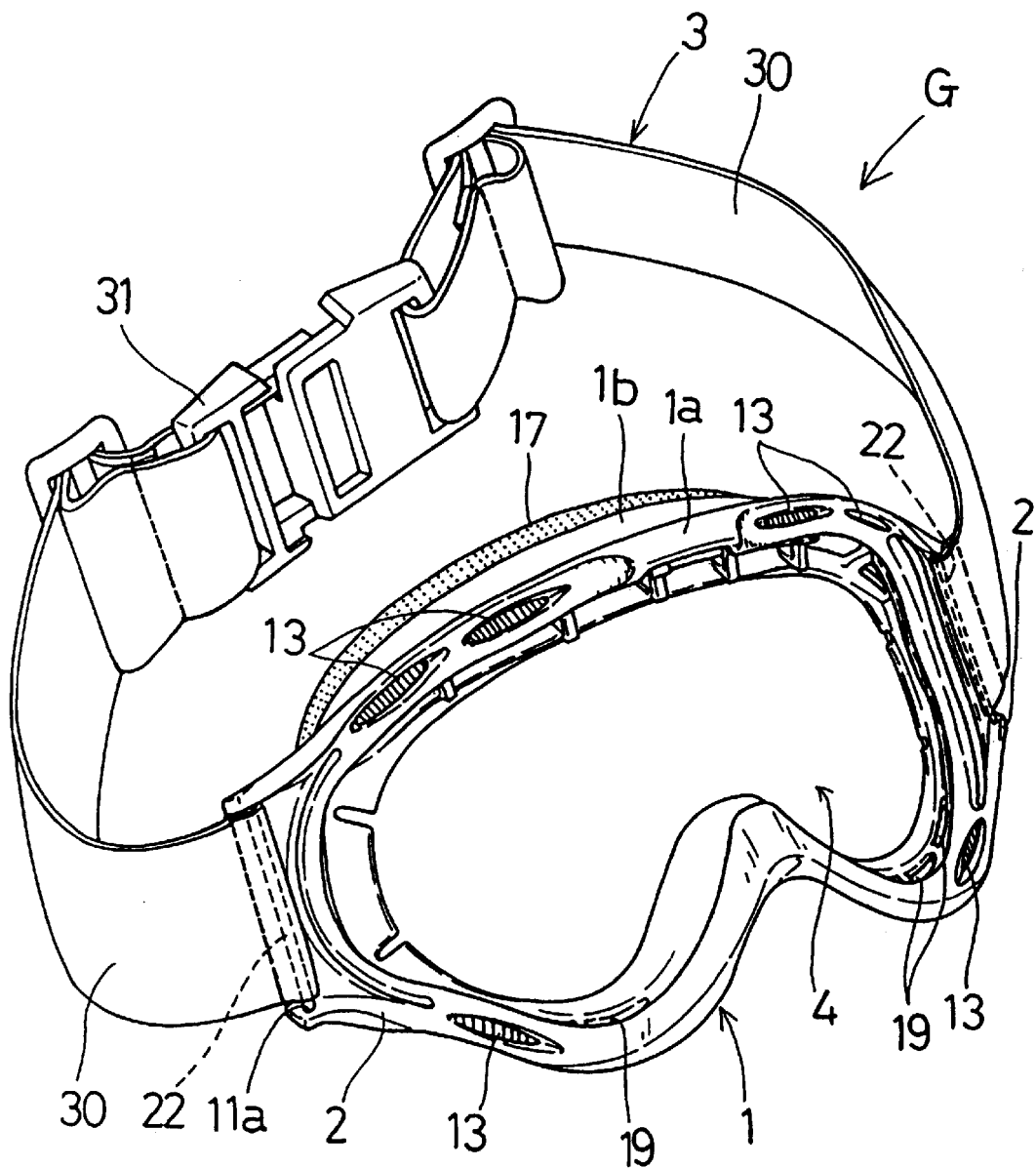
FIG. 1 is a perspective view of goggles in one embodiment of the present invention.
Figure 2:
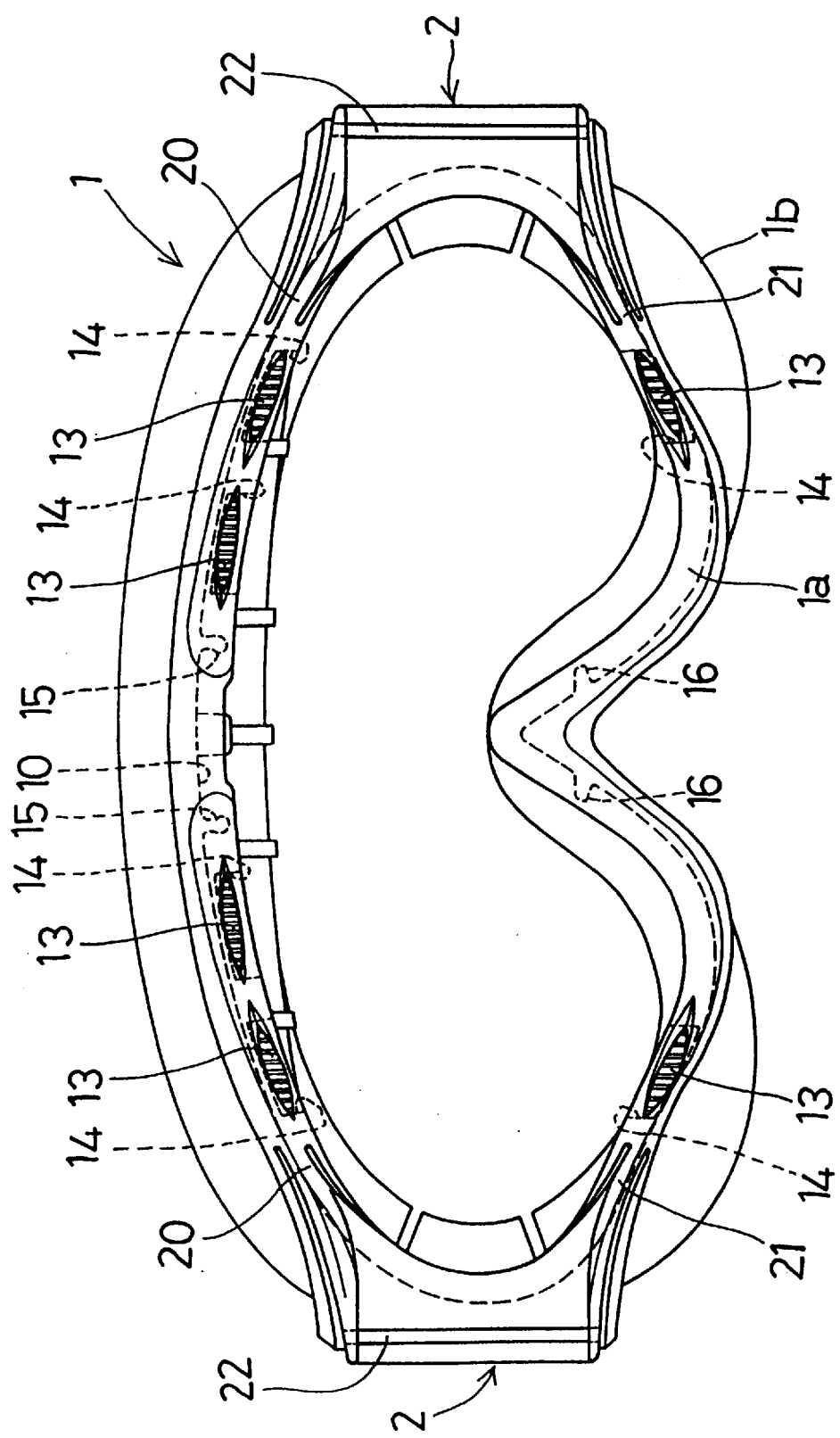
FIG. 2 is a front view of the goggles.

FIG. 1 is a perspective view of skiing goggles G. FIG. 2 is a front view of a goggle frame 1 of the goggles G. As shown in FIGS. 1 and 2, the goggles G include a goggle frame 1, arms 2 provided on the right and left end portions of the goggles frame 1, an expandable, elastic band 3 coupled to the goggle frame 1, and a goggle lens 4 detachably fitted into the goggle frame 1.

Figure 3:
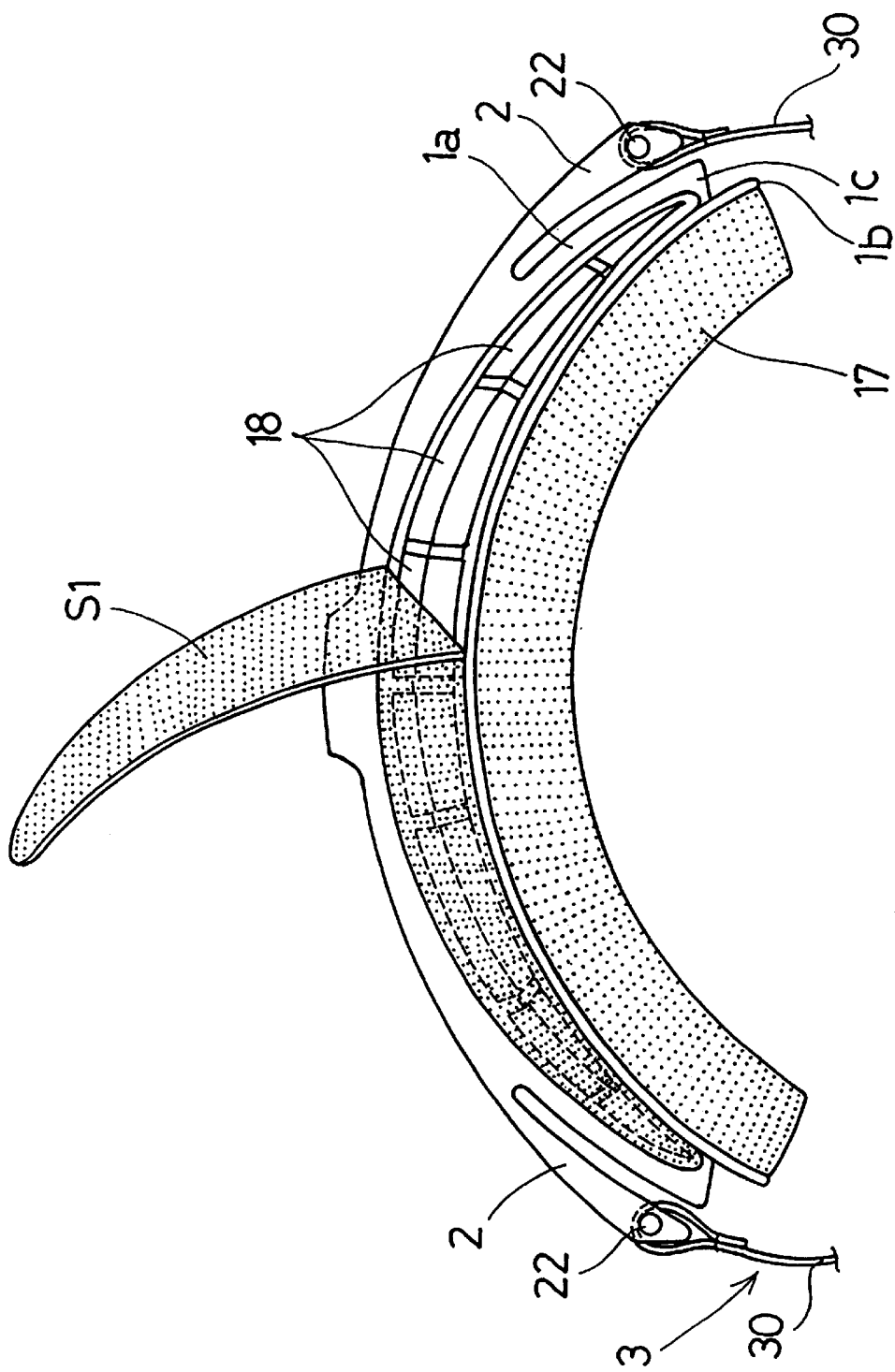
FIG. 3 is a top view of the goggles.
Figure 7:
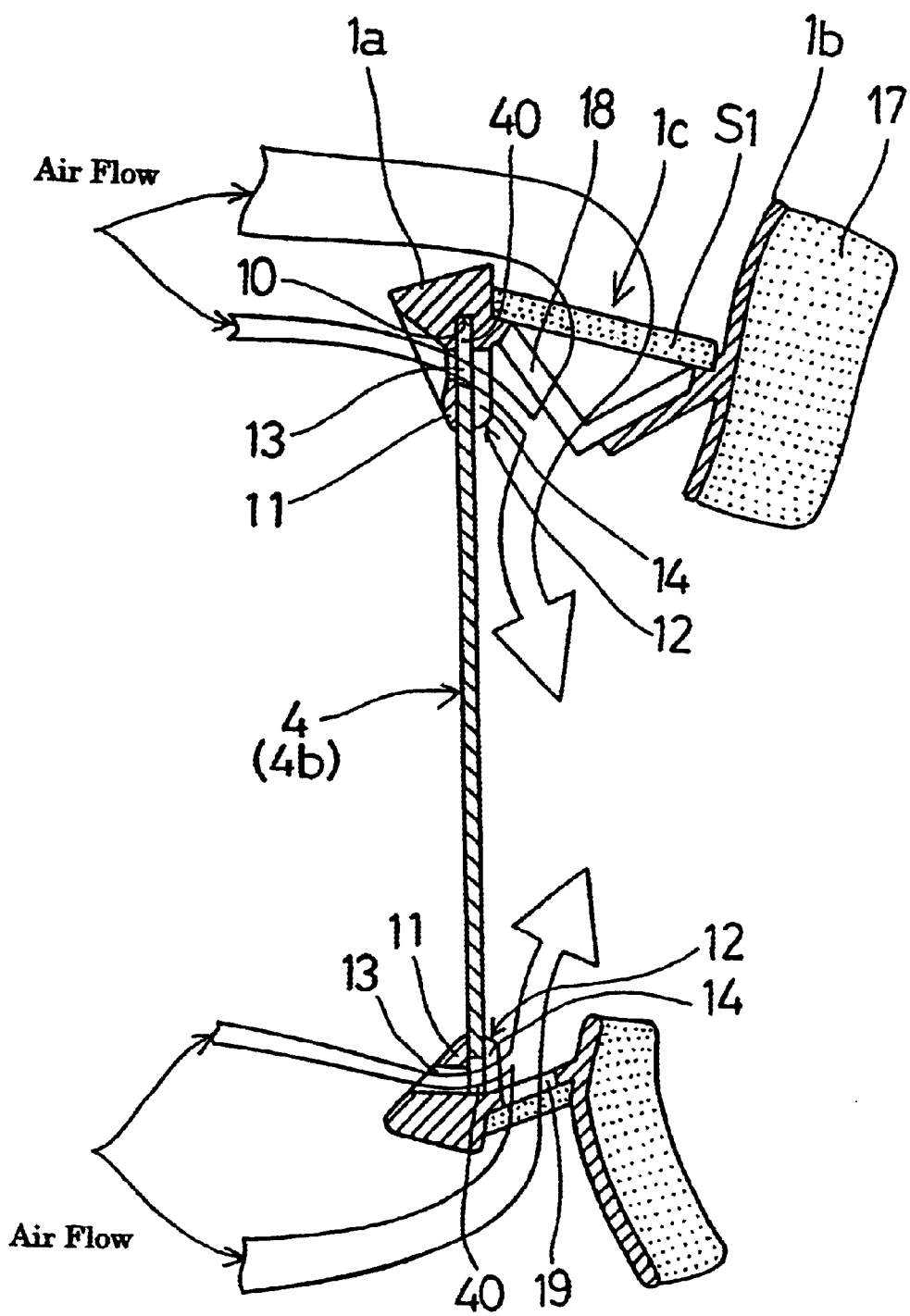
FIG. 7 is a section view showing air-flow in case a goggle lens for general use is fitted in the goggle frame.

The goggle frame 1 is made of soft material such as an elastic synthetic resin, rubber or the like. As shown in FIGS. 1, 3 and 7, the goggle frame 1 includes a lens fitting edge 1a, a face abutment section 1b and a peripheral wall section 1c connecting the lens fitting edge 1a to the face abutment section 1b. The goggle lens 4 is detachably fitted into the lens fitting edge 1a.

Figure 6:
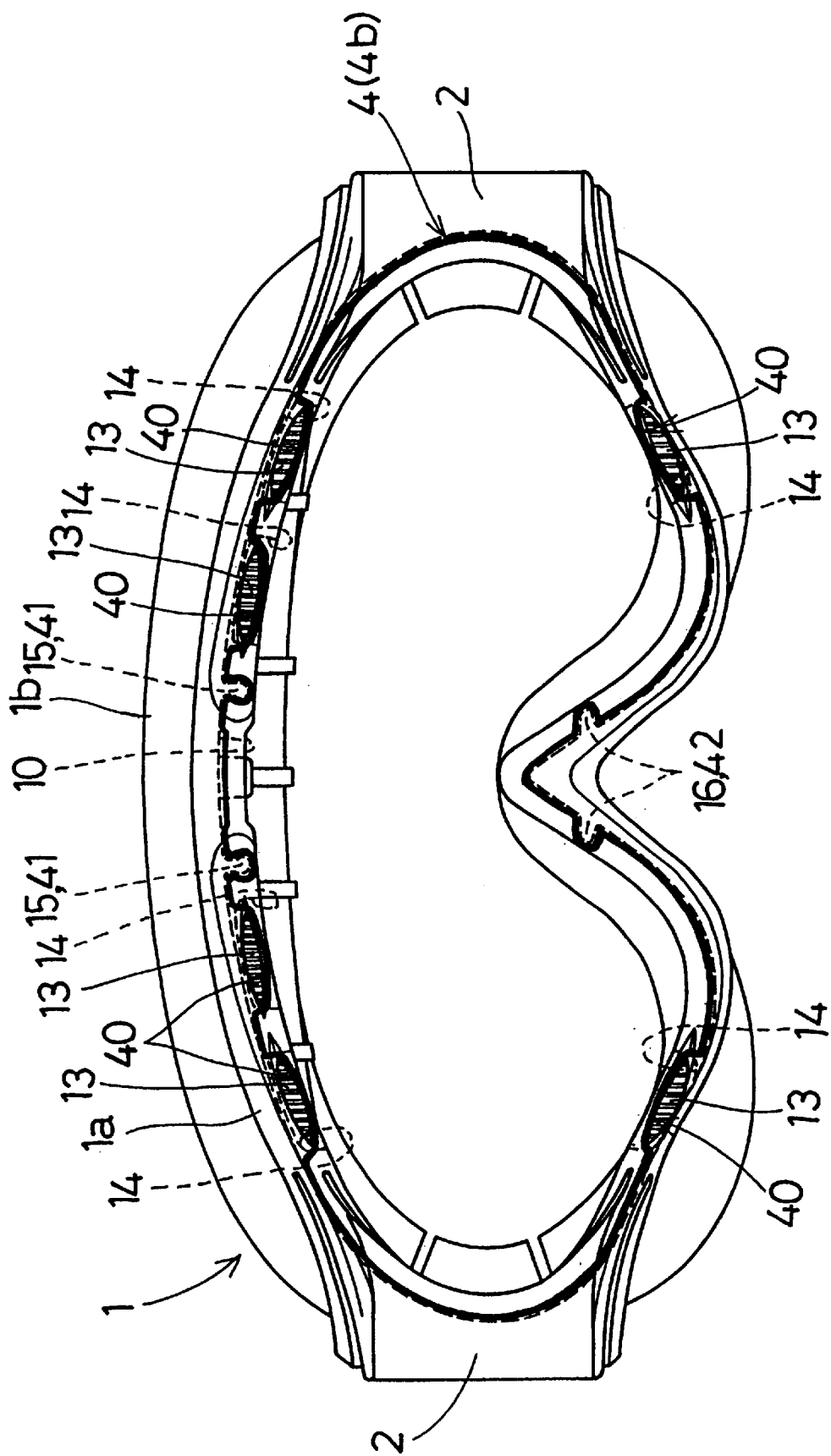
FIG. 6 is a front view showing the goggles with a goggle lens for general use fitted in the goggle frame.

As shown in FIG. 6, the lens fitting edge 1a is provided with a groove 10 in which an outer peripheral edge of the goggle lens 4 is received. The groove 10 is constituted with a front wall 11 and a rear wall 12 (FIGS. 7 and 8) in which ventilation openings 13 and 14 are respectively provided. In this embodiment, as shown in FIGS. 2 and 7, the opening 13 of the front wall 11 is formed in a oval shape in a front view and provided with vertical gratings. The opening 14 of the rear wall is formed by cutting. In the groove 10, as shown in FIG. 2, is provided with protrusions 15 and 16 for positioning the goggle lens 4 and preventing removal of it.

The face abutment section 1b, as shown in FIGS. 1 and 3, is provided with a close contact material 17 such as sponge or monte plane in order to give comfortable close fitting to a wearer's face.

The peripheral wall section 1c, as shown in FIGS. 1 to 3, is provided with ventilation sections 18 and 19 formed with plural holes on the upper and lower constitutional walls. The ventilation sections 18 and 19 are respectively designed to be closed by and covered with thin sponge plates S1 and S2. The reason for closing and covering the ventilation sections 18 and 19 by the sponge plates S1 and S2 is to prevent snow and/or dust other than air from entering inside of the goggles.

Figure 4:
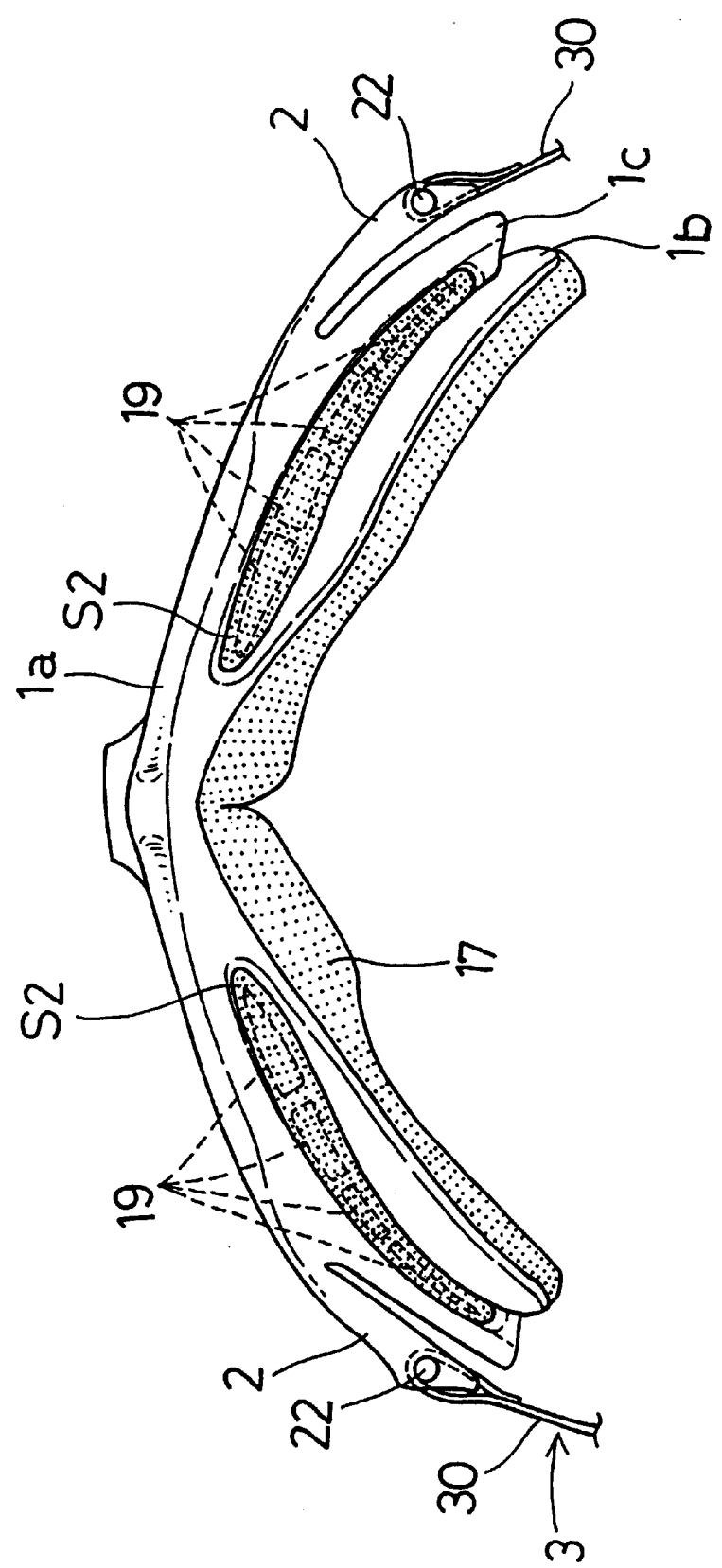
FIG. 4 is a bottom view of the goggles.

The arms 2 are formed with the goggle frame 1 in one body. As shown in FIGS. 2 to 4, the arms 2 are shaped matching with the shape of the right and left end portions of the front face of the lens fitting edge 1a. One end 20 of each arm 2 extends outwardly from the front face of the upper portion of the frame of the lens fitting edge 1a and the other end 21 thereof extends outwardly from the front face of the lower portion of the frame of the lens fitting edge 1a. The arms 2 in a non-used state extend substantially along with the front face of the upper and lower portions of the frame of the lens fitting edge 1a. As seen from FIG. 2, the arms 2 do not stand within the goggle frame 1 in a front view. The arms 2 have positions to receive the expandable, elastic belt 3 at their free ends. More concretely, as shown in FIGS. 2 and 3, the expandable, elastic band 3 is attached to the each arm 2 in a fashion that the end portion of the band 3, forming a cylindrical shape, surrounds a bar 22. The expandable, elastic band 3 includes band bodies 30 and 30 which are made elastic. They are attached to respective arms 2 and designed to be coupled together by means of a buckle 31.

The goggle lens 4 is made of synthetic resin plate (cellulouse propionate, triacetate, polycarbonate and the like) and has a high anti-scratch property and prevents ultra violet rays. And the inside surface of the lens is provided with an anti-fog treatment.

Figure 5:
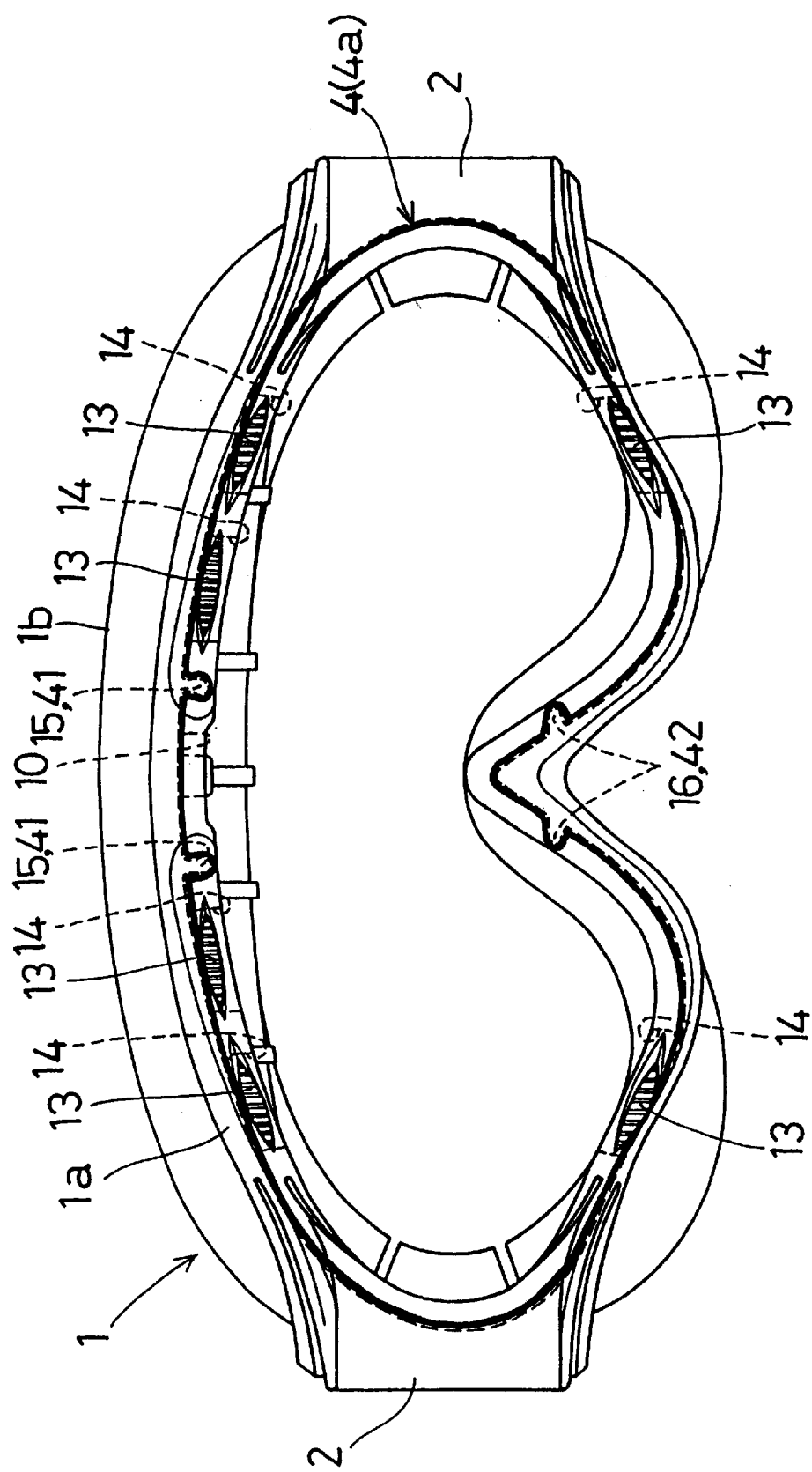
FIG. 5 is a front view showing the goggles with a goggle lens for a competition fitted in the goggle frame.

For the goggles G in this embodiment, a goggle lens 4a for a competition, shown with the thick line in FIG. 5, and a goggle lens 4b for general use, shown with the thick line in FIG. 6, are prepared.

Figure 8:
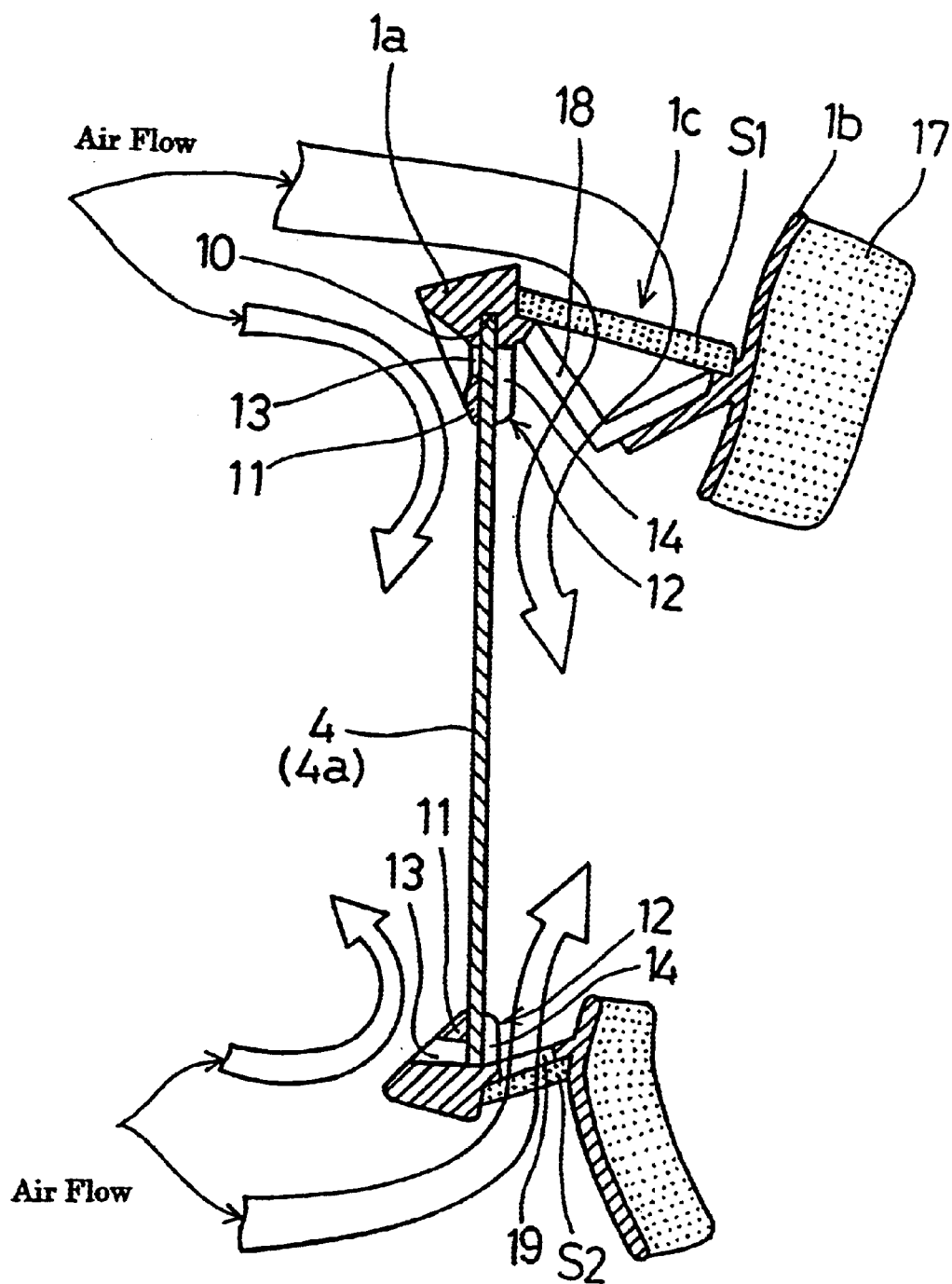
FIG. 8 is a section view showing air-flow in case a goggle lens for competition use is fitted in the goggle frame.

The thick line in FIG. 5 shows the outline of the goggle lens 4a for a competition. In a state where the lens 4a is fitted in the groove 10 of the lens fitting edge 1a, as shown in FIGS. 5 and 8, the opening 14 of the rear wall 12 is covered.

The thick line in FIG. 6 shows the outline of the goggle lens 4b for general use. The lens 4b has cuttings 40 at the positions corresponding to the openings 13 and 14. Therefore, in the state where the lens 4b is fitted in the groove 10 of the lens fitting edge 1a, as shown in FIGS. 6 and 7, the openings 13 and 14 of the front and rear walls 11, 12 are communicating with each other through the cuttings 40.

The goggle lenses 4a and 4b, as shown in FIGS. 5 and 6, respectively have recesses 41 and 42 matching with the foregoing protrusions 15 and 16. The stopping force between the protrusions 15 and 16 and the recesses 41 and 42 reliably fixes the goggle lens 4a or 4b at the certain position of the goggle frame 1.

When the goggle lens 4a for a competition is set to the goggle, as stated above, the opening 14 of the rear wall 12 is covered by the goggle lens 4a and the amount of air-flow into inside of the goggle lens 41 lessens so that the influence of wind against the eyes of a wearer can be alleviated.

When the goggle lens 4b for general use is set to the goggle, as stated above, the openings 13 and 14 of the front and rear walls 11 and 12 are communicating with each other, and the amount of air-flow into inside of the goggle lens 4b increases so that anti-fog effect is enhanced.

In the goggles of this embodiment, the ventilation section is formed on the goggle frame 1 per se. Thus no ventilation section is added within the area of the goggle frame 1 which was described in the section of Prior Art. Therefore the field of vision is not narrowed.

The present invention should not be limited to the above embodiment. In addition to the goggle lenses 4a and 4b, a goggle lens 4 which has smaller cuttings than those of the goggle lens 4b may be prepared for the goggle. When this goggle lens 4 is set to the goggle frame 1, the amount of air-flow into inside of the goggle lens 4 can be controlled in a middle degree between those of the goggle lenses 4a and 4b. Therefore, provision of goggle lenses with cuttings in varying sizes allows to control the amount of air-flow into inside of the goggle lenses.

The opening 13 in the above embodiment may be covered with and closed by a sponge plate as a filter. Furthermore, the shape and size of the openings 13 of the front wall 11 and those of the openings 14 of the rear wall 12 can be freely determined.

The goggles of the present invention are not limited to ski goggles, but can be applied to goggles for other purposes, such as dust-protective goggles, goggles used for cold weather districts.

With the construction stated above, the present invention can provide goggles in which the wide field of vision can be guaranteed without enlarging the goggle frame and the amount of air-flow from the ventilation sections can be easily controlled.

What is claimed is:

1. Goggles comprising:

a goggle frame;

a groove formed on an inner peripheral portion of said goggle frame, said groove having a front wall and a rear wall;

ventilation openings being opposingly provided on said front wall and said rear wall; and a goggle lens being one of at least first and second goggle lenses, said first goggle lens having openings therein which align with said ventilation openings in said front and rear walls and said second goggle lens having no openings therein;

wherein said groove is selectively receivable of any one of a said second goggle lens which covers said ventilation openings of said rear wall and a said first goggle lens which allows the ventilation openings on said front and rear walls to communicate with each other.

2. Goggles according to claim 1, wherein said ventilation opening of said front wall is a hole with plural gratings.

3. Goggles according to claim 1, wherein said ventilation opening of said front wall is covered with a filter.

4. Goggles according to claim 1, wherein said openings of said first goggle lens are cut-out openings formed by peripheral portions being cut out.

5. Goggles according to claim 4, wherein said ventilation opening of said front wall is a hole with plural gratings.

6. Goggles according to claim 4, wherein said ventilation opening of said front wall is covered with a filter.

7. Goggles according to claim 4 wherein sizes of the cut-out openings vary among plural of said first goggle lenses and by changing first goggle lenses to be fitted into said groove of said goggle frame, an amount of air-flow into inside of said goggles is changeable.

8. Goggles according to claim 7, wherein said ventilation opening of said front wall is a hole with plural gratings.

9. Goggles according to claim 7, wherein said ventilation opening of said front wall is covered with a filter.

* * * * *